(12) United States Patent
Craven (10) Patent No.: US 10,288,626 B2
(45) Date of Patent: May 14, 2019

(54) SECRETED TUMOR-ASSOCIATED CYTOCHROME AS A BLOOD-BASED BIOMARKER FOR CANCER

(71) Applicant: University of Kentucky Research Foundation, Lexington, KY (US)

(72) Inventor: Rolf Joseph Craven, Lexington, KY (US)

(73) Assignee: University of Kentucky Research Foundation, Lexington, KY (US)

(*) Notice: Subject to any disclaimer, the term of this patent is extended or adjusted under 35 U.S.C. 154(b) by 57 days.

(21) Appl. No.: 14/028,224

(22) Filed: Sep. 16, 2013

(65) Prior Publication Data

US 2014/0106375 A1 Apr. 17, 2014

Related U.S. Application Data

(60) Provisional application No. 61/701,449, filed on Sep. 14, 2012.

(51) Int. Cl.
*G01N 33/68* (2006.01)
*G01N 33/574* (2006.01)
*G01N 33/74* (2006.01)

(52) U.S. Cl.
CPC ... *G01N 33/6893* (2013.01); *G01N 33/57407* (2013.01); *G01N 33/57423* (2013.01); *G01N 33/743* (2013.01); *G01N 2800/50* (2013.01); *G01N 2800/52* (2013.01)

(58) Field of Classification Search
None
See application file for complete search history.

(56) References Cited

U.S. PATENT DOCUMENTS

| 4,230,797 | A | 10/1980 | Boguslaski et al. |
| 4,233,402 | A | 11/1980 | Maggio et al. |
| 4,275,149 | A | 6/1981 | Litman et al. |
| 4,376,110 | A | 3/1983 | David et al. |
| 4,659,678 | A | 4/1987 | Forrest et al. |
| 4,727,022 | A | 2/1988 | Skold et al. |
| 2009/0176228 | A1* | 7/2009 | Birse et al. ............ 435/6 |

FOREIGN PATENT DOCUMENTS

| WO | WO 01/31579 | 5/2001 |
| WO | WO 02/06829 | 1/2002 |
| WO | WO 02/42733 | 5/2002 |

OTHER PUBLICATIONS

Rohe et al. (Pharmacology and Therapeutics, 121: 14-19, 2009).*
Ahmed et al. (Journal of Pharmacology and Experimental Therapeutics, 333(2): 564-573, 2010).*
Mir et al. (International Journal of cancer, 131: E1-E9, available online Sep. 14, 2011).*
Mir et al. (Int. J. Cancer, 131: e1-e9, 2012, available online: Sep. 14, 2011).*
Théry et al. (Current Protocols in Cell Biology, 30(1): 3.22.1-3.22.29, 2006).*
Gazdar, AF., "Activating and Resistance Mutations of EGFR in Non-Small-Cell Lung Cancer: Role in Clinical Response to EGFR Tyrosine Kinase Inhibitors", NIH Public Access, Aug. 2009, pp. 1-14, 28 Suppl 1: S24-31, Oncogene.
Lynch, Thomas J. et al., "Activating Mutations in the Epidermal Growth Factor Receptor Underlying Responsiveness of Non-Small-Cell Lung Cancer to Gefitinib", The New England Journal of Medicine, May 2004, pp. 2129-2139, vol. 350, No. 21, Massachusetts Medical Society.
Pao, William et al., "EGF Receptor Gene Mutations are Common in Lung Cancers From "Never Smokers" and are Associated With Sensitivity of Tumors to Gefitinib and Erlotinib", Proceedings of the National Academy of Sciences, Sep. 2004, pp. 13306-13311, vol. 101, No. 35, The National Academy of Sciences.
Hughes, Adam L. et al., "Dap1/PGRMC1 Binds and Regulates Cytochrome P450 Enzymes", Cell Metabolism, Feb. 2007, pp. 143-149, vol. 5, Cell Press.
Ahmed, Ikhlas S. et al., "Pgrmc1 (Progesterone Receptor Membrane Component 1) Associates with Epidermal Growth Factor Receptor and Regulates Erlotinib Sensitivity", The Journal of Biological Chemistry, Aug. 2010, pp. 24775-24782, vol. 285, No. 32, The American Society for Biochemistry and Molecular Biology, Inc.
Crudden, Gerard et al., "Hpr6 (Heme-1 Domain Protein) Regulates the Susceptibility of Cancer Cells to Chemotherapeutic Drugs", The Journal of Pharmacology and Experimental Therapeutics, 2006, pp. 448-455, vol. 316, No. 1, The American Society for Pharmacology and Experimental Therapeutics.
Nolte, I. et al., "Localization and Topology of Ratp28, a Member of a Novel Family of Putative Steroid-Binding Proteins", Biochemica et Biophysica Acta, 2000, pp. 123-130, vol. 1543, Elsevier.
Peluso, "John J. et al., Progesterone Receptor Membrane Component-1 (PGRMC1) Is the Mediator Progesterone's Antiapoptotic Action in Spontaneously Immortalized Granulosa Cells As Revealed by PGRMC1 Small Interfering Ribonucleic Acid Treatment and Functional Analysis of PGRMC1 Mutations", Endocrinology, 2008, pp. 534-543, vol. 149, No. 2, The Endocrine Society.
Min, Li et al., "Molecular Identification of Adrenal Inner Zone Antigen as a Heme-Binding Protein", The FEBS Journal, 2005, pp. 5832-5843, vol. 272, FEBS.
Mifsud, William et al., "Membrane-Bound Progesterone Receptors Contain a Cytochrome belike Ligand-Binding Domain", Genome Biology, Nov. 2002, pp. 1-5, vol. 3, No. 12, Research 0068.

(Continued)

*Primary Examiner* — Nelson B Moseley, II
(74) *Attorney, Agent, or Firm* — Crowell & Moring LLP (57) ABSTRACT

Disclosed herein are methods for detecting Pgrmc1 in bodily fluids, e.g., blood, plasma and serum, wherein detection of Pgrmc1 is a biomarker for the presence of cancer, e.g., lung cancer or head or neck cancer. Pgrmc1 levels in bodily fluids may be used to predict patient prognosis, e.g., survival and response to therapy.

17 Claims, 6 Drawing Sheets
Specification includes a Sequence Listing.

(56) References Cited

OTHER PUBLICATIONS

Cahill, Michael A., "Progesterone Receptor Membrane Component 1: An Integrative Review", The Journal of Steroid Biochemistry & Molecular Biology, 2007, pp. 16-36, vol. 16, Elsevier.
Crudden, Gerard et al., "Overexpression of the Cytochrome P450 Activator Hpr6 (Heme-1 Domain Protein/Human Progesterone Receptor) in Tumors", TumorBiology, 2005, pp. 142-146, vol. 25, Karger AG, Basel.
Neubauer, Hans et al., "Breast Cancer proteomics Reveals Correlation Between Estrogen Receptor Status and Differential Phosphorylation of PGRMC1", Breast Cancer Research, 2008, vol. 10, No. 5, BioMed Central Ltd.
Peluso, John J. et al., "Regulation of Ovarian Cancer Cell Viability and Sensitivity to Cisplatin by Progesterone Receptor Membrane Component-1", The Journal of Endocrinology Metabolism, May 2008, pp. 1592-1599, vol. 93, No. 5, The Endocrine Society.
Irby, Rosalyn B. et al., "Iterative Microarray and RNA Interference-Based Interrogation of the Src-Induced Invasive Phenotype", Cancer Research, Mar. 2005, pp. 1814-1821, vol. 65, No. 5, The American Association for Cancer Research.
Difilippantonio, S. et al., "Gene Expression Profiles in Human Non-Small and Small-Cell Lung Cancers", European Journal of Cancer, 2003, pp. 1936-1947, vol. 39, Elsevier Science Ltd.
Selmin, Ornella et al., "Isolation and Characterization of a Novel Gene Induced by 2,3,7,8-tetrachlorodibenzo-p-dioxin in Rat Liver".
Nie, Alex Y. et al., "Predictive Toxicogenomics Approaches Reveal Underlying Molecular Mechanisms of Nongenotoxic Carcinogenicity", Molecular Carcinogenesis, 2006, pp. 914-933, vol. 45, Wiley InterScience.
Ahmed, Ikhlas S. et al., "Progesterone Receptor Membrane Component 1 (Pgrmc1): A Heme-1 Domain Protein That Promotes Tumorigenesis and Is Inhibited by a Small Molecule", The Journal of Pharmacology and Experimental Therapeutics, 2010, pp. 564-573, vol. 333, No. 2, The American Society for Pharmacology and Experimental Therapeutics.
Peluso, John J. et al., "Progesterone Receptor Membrane Component-1 Regulates the Development and Cisplatin Sensitivity of Human Ovarian Tumors in Athymic Nude Mice", Endocrinology, Nov. 2009, pp. 4846-4854, vol. 150, No. 11, The Endocrine Society.
Peluso, John J. et al., "Progesterone Membrane Receptor Component 1 Expression in the Immature Rat Ovary and Its Role in Mediating Progesterone's Antiapoptotic Action", Endocrinology, 2006, pp. 3133-3140, vol. 147, No. 6, The Endocrine Society.
Lodde, Valentina et al., "A Novel Role for Progesterone and Progesterone Receptor Membrane Component 1 in Regulating Spindle Microtubule Stability During Rat and Human Ovarian Cell Mitosis", Biology of Reproduction, Dec. 2010, pp. 715-722 vol. 84, The Society for the Study of Reproduction, Inc.
Yoshitani, Naoei et al., "A Structure-Based Strategy for Discovery of Small Ligands Binding to Functionally Unknown Proteins: Combination of in Silico Screening and Surface Plasmon Resonance Measurements", Proteomics, 2005, pp. 1472-1480, vol. 5, WILEY-VCH Verlag GmbH & Co. KGaA, Weinheim.
Wirth, Urs et al., "Post-Translational Modification Detection Using Metastable Ions in Reflector Matrix-Assisted Laser Desorption/ionization-time of Flight Mass Spectrometry", Proteomics, 2002, pp. 1445-1451, vol. 2, WILEY-VCH Verlag GmbH & Co. KGaA, Weinheim.
Kimura, Ikuo et al., "Neurotrophic Activity of Neudesin, a Novel Extracellular Heme-binding Protein, Is Dependent on the Binding of Heme to Its Cytochrome b5-like Heme/Steroid-binding Domain", The Journal of Biological Chemistry, Feb. 2008, pp. 4323-4331, vol. 283, No. 7, The American Society for Biochemistry and Molecular Biology, Inc.
Kimura, Ikuo et al., "Neuferricin, a Novel Extracellular Heme-Binding Protein, Promotes Neurogenesis", Journal of Neurochemistry, 2010, pp. 1156-1157, vol. 112, International Society for Neurochemistry.
Kimura, Ikuo et al., "Neudesin, a Novel Secreted Protein With a Unique Primary Structure and Neurotrophic Activity", Journal of Neuroscience Research, 2005, pp. 287-294, vol. 79, Wiley-Liss, Inc.
Marek, Carytyn J. et al., "Low Affinity Glucocorticoid Binding Site Ligands as Potential Anti-Fibrogenics", Comparative Hepatology, 2009, vol. 8, No. 1, BioMed Central Ltd.
Roy et al., "Proteomic Analysis of the Transitional Endoplasmic Reticulum in Hepatocellular Carcinoma: An Organelle Perspective on Cancer", Biochimica et Biophysica Acta, Sep. 2010, pp. 1869-1881, vol. 1804, No. 9, Elsevier.
Krebs, Christopher J. et al., "A Membrane-Associated Progesterone-Binding Protein, 25-Dx, Is Regulated by Progesterone in Brain Regions Involved in Female Reproductive Behaviors", Proceedings of the National Academy of Sciences, Nov. 2000, pp. 12816-12821, vol. 97, No. 23.
Shin, Bong Kyung et al., "Global Profiling of the Cell Surface Proteome of Cancer Cells Uncovers an Abundance of Proteins with Chaperone Function", The Journal of Biological Chemistry, Feb. 2003, pp. 7607-7616, vol. 278, No. 9, The American Society for Biochemistry and Molecular Biology, Inc.
Labombarda, F. et al., "Effects of Injury and Progesterone Treatment on Progesterone Receptor and Progesterone Binding Protein 25-Dx Expression in the Rat Spinal Cord", Journal of Neurochemistry, 2003, pp. 902-913, vol. 87, International Society for Neurochemistry.
Mallory, Julia C. et al., "A Novel Group of Genes Regulates Susceptibility to Antineoplastic Drugs in Highly Tumorigenic Breast Cancer Cells", Molecular Pharmacology, 2005, pp. 1747-1756, vol. 68, No. 6, The American Society for Pharmacology and Experimental Therapeutics.
Hand, Randal A. et al., "Hpr6.6 Protein Mediates Cell Death From Oxidative Damage in MCF-7 Human Breast Cancer Cells", Journal of Cellular Biochemistry, 2003, pp. 534-547, vol. 90, Wiley-Liss, Inc.
Ichinose, Yukito et al., "Prognostic Factors Obtained by a Pathologic Examination in Completely Resected Non-Small-Cell Lung Cancer", Journal of Thoracic Cardiovascular Surgery, 1995, pp. 601-605, vol. 110, No. 3, Mosby-Year Book, Inc.
Takise, Atsushi et al., "Histopathologic Prognostic Factors in Adenocarcinomas of the Peripheral Lung Less Than 2 cm in Diameter", May 1988, Cancer, pp. 2083-2088, vol. 61, No. 10.

* cited by examiner

A. plasma S2R by stage

C. adeno tumor S2R by stage

B. plasma S2R by stage

D. squamous tumor S2R by stage

FIG 6

SECRETED TUMOR-ASSOCIATED CYTOCHROME AS A BLOOD-BASED BIOMARKER FOR CANCER

RELATED APPLICATIONS

This application claims priority under 35 U.S.C. 119(e) to provisional application No. 61/701,449 filed Sep. 14, 2012, the disclosure of which is incorporated herein in its entirety.

BACKGROUND OF THE INVENTION

The present invention relates generally methods for the detection and diagnosis of cancer in a subject. More particularly, the invention relates to methods and kits for detecting Pgrmc1 (progesterone receptor membrane component 1) in a bodily fluid sample to facilitate the detection and diagnosis of cancer, particularly lung cancer.

Cancer is one of the leading causes of death, and there is an urgent need for new biomarkers and therapeutic targets and method for early detection of cancer. Lung cancer is the leading cause of cancer death worldwide, resulting in 150,000 deaths per year in the United States. The mortality rate from lung cancer is greater than the combined mortality from breast, prostate and colorectal cancers. On the basis of morphology, lung cancer can be broadly classified into four main categories namely, adenocarcinoma, squamous cell carcinoma, large cell undifferentiated carcinoma and small cell carcinoma. Both squamous cell carcinoma and small cell carcinoma are strongly associated with a smoking history.

Adenocarcinoma, squamous cell carcinoma, and large cell undifferentiated carcinoma are usually referred as "non-small cell carcinoma." They are relatively chemo-resistant, and hence the mainstay of treatment is surgery. By contrast, small cell carcinoma has a higher propensity for distant metastases and is mainly treated by chemotherapy.

While biopsy can be used to diagnose various cancers, it is an invasive procedure and, therefore, less than desirable. Other diagnostic methods for cancers include ultrasound and computed tomography (CT) scan. Nonetheless, methods and kits for detecting biomarkers associated with cancer, particularly biomarkers present in a blood or serum sample, are urgently needed to facilitate early detection and treatment of cancer.

EGFR (epidermal growth factor receptor) is one of the most promising therapeutic targets in lung cancer, and EGFR inhibitors have produced positive clinical results, particularly for patients with activating mutations in the EGFR kinase domain (Gazdar A F., Oncogene 2009,28 Suppl 1:S24-31; Lynch et al., The New England Journal of Medicine 2004; 350:2129-39; Pao et al., Proc Natl Acad Sci USA 2004; 101:13306-11).

Pgrmc1 (progesterone receptor membrane component) is a microsomal protein that colocalizes with EGFR in the endoplasmic reticulum or punctate cytoplasmic sites. Pgrmc1 associates with EGFR in lung cancer cells and increases susceptibility to the EGFR inhibitor erlotinib, it is also a cytochrome b5 related protein. (Hughes et al., Cell Metab 2007; 5:143-9; Ahmed et al., J Biol Chem 2010, 285:24775-82; Crudden, Chitti and Craven R J., J Pharmacol Exp Ther 2006, 316:448-55; Nolte et al., Biochim Biophys Acta 2000; 1543:123-30; Peluso, Romak, and Liu, Endocrinology 2008; 149:534-43; Min et al., FEBS J 2005, 272:5832-43; Mifsud and Bateman, Genome Biol 2002, 3: RESEARCH0068; Cahill, J Steroid Biochem Mol Biol 2007, 105:16-36). Recently, Pgrmc1 was identified as a sigma-2 receptor (S2R), with a clear role in tumor cell survival.

Pgrmc1 is also induced in multiple tumor types. For example, Pgrmc1 is induced in approximately approximately one-half of breast tumors compared to matched nonmalignant tissue, and Pgrmc1 is enriched in estrogen receptor-negative breast tumors (Crudden et al., Tumour Biol 2005, 26:142-6; Neubauer et al., Breast Cancer Res 2008, 10:R85). In ovarian cancer, Pgrmc1 expression increases with tumor stage, and Pgrmc1 is also enriched in colon and lung cancers (Peluso et al., J Clin Endocrinol Metab 2008, 93:1592-9; Letwin et al., Cancer Res 2005 65:1814-21; Irby et al., Cancer Res 2005, 65:1814-21; Difilippantonio et al., Eur J Cancer 2003; 39:1936-47). The mechanism through which Pgrmc1 is induced in tumors is unclear, but may include induction by carcinogenic compounds (Difilippantonio 2003; Selmin et al., Carcinogenesis 1996; 17:2609-15; Nie et al., Mol Carcinog 2006; 45:914-33). Pgrmc1 is inhibited by a small molecule ligand called AG-205, which inhibits growth in tumor cells and decreases EGFR levels (Ahmed et al., J Pharmacol Exp Ther 2010, 333:564-73; Ahmed et al., J Biol Chem 2010, 285:24775-82). Pgrmc1 also contributes to multiple features of tumor growth. In lung adenocarcinoma cells, Pgrmc1 promotes proliferation, anchorage-independent growth, migration, primary tumor growth and metastasis (Ahmed et al., J Pharmacol Exp Ther 2010). Pgrmc1 has a similar biological role in ovarian cancer, where it regulates tumor growth as well as angiogenesis and tumor pathology (Peluso et al., Endocrinology 2009, 150:4846-54). Pgrmc1 also suppresses apoptosis in immortalized granulosa and ovarian cancer cells (Peluso et al., Endocrinology 2006, 147:3133-40; Peluso et al., J Clin Endocrinol Metab 2008, 93:1592-9) and contributes to mitotic progression in ovarian cancer (Lodde et al., Biol Reprod 2010, 84:215-222). Pgrmc1 is inhibited by a small molecule ligand called AG-205, which inhibits growth in tumor cells and decreases EGFR levels (Yoshitani et al., Proteomics 2005, 5:1472-80; Ahmed et al., J Pharmacol Exp Ther 2010; Ahmed et al., J Biol Chem 2010.

SUMMARY OF THE INVENTION

The invention described herein relates to methods that facilitate the diagnosis of cancer in a subject, determining the stage of the cancer, and determining the prognosis for and/or treatment of a subject having a cancer, e.g., a lung cancer. Prior to this invention Pgrmc1 was not known to be a secreted protein and was not detected in bodily fluids, e.g. blood, plasma or serum, or in subfractions of such fluids, e.g., exosome-containing fractions. Thus, secreted Pgrmc1 is a biomarker for detecting the presence of cancer in a subject and for monitoring cancer progression in a subject by assaying its levels in a bodily fluid.

An aspect of this invention is a method for detecting cancer in a subject by measuring the levels of Pgrmc1 in a bodily fluid, wherein the level of Pgrmc1 in a bodily fluid facilitates determining whether a subject has a cancer. Measuring the levels of Pgrmc1 in a bodily fluid is also useful in assessing the stage of the cancer, particularly stage 1 lung cancer where the cancer limited to the lung and hasn't spread to the lymph nodes and wherein the tumor is generally smaller, e.g., less than about 2 inches (5 centimeters) across. Also described herein are methods for monitoring the progression of a cancer in a subject.

Thus the methods of the invention can also be used to assess cancer status, particularly lung cancer status, in a subject. "Cancer status" in the context of the present invention includes, inter alia, the presence or absence of disease, the risk of developing disease, the stage of the disease, and the effectiveness of treatment of disease. Based on this status, further procedures may be indicated, including additional diagnostic tests or therapeutic procedures or regimens, such as endoscopy, biopsy, surgery, chemotherapy, immunotherapy, and radiation therapy.

The invention also contemplates a kit for use in detecting and diagnosing cancer in a subject, thereby assessing cancer status in a subject. Kits within the invention comprise, for example, and antibody that specifically binds to Pgrmc1, e.g., a polyclonal or monoclonal antibody that binds to native Pgrmc1, or denatured Pgrmc1, preferably an antibody that binds to a native Pgrmc1, and directions for detecting Pgrmc1 in a bodily fluid sample. The kit may also include a control reference, indicating the levels of Pgrmc1 in a subject without cancer (a negative control reference) or indicating the levels of Pgrmc1 in a subject with a cancer (a positive control reference). The positive control references may indicate the levels of Pgrmc1 in subjects having a cancer, e.g., a lung cancer, a breast cancer, an ovarian cancer, an oral cancer or a head or neck cancer.

BRIEF DESCRIPTION OF THE DRAWINGS

FIG. 1 depicts elevated Pgrmc1 expression in tumors of matched squamous cell lung carcinoma (SCLC) clinical samples. (A) Pgrmc1 expression was determined by western blot in non-malignant tissue (gray bars) and paired tumors (black bars) from the same patient. The Y-axis refers to the fold change relative to a non-malignant tissue sample that was included in each western blot. Analyses were performed in triplicate, and Pgrmc1 was significantly elevated in 12/15 samples. Throughout, $*=\leq 0.05$, $=\leq 0.01$ and $*\leq=0.005$. (B) A Pgrmc1-specific antibody recognized elevated Pgrmc1 expression in an SCLC tumor (upper panel, lane 2) compared to matched normal tissue (upper panel, lane 1). The migration of molecular weight markers is indicated on the left of the figure. The 25 kDa reactive band was blocked by the addition of immunogenic peptide (second panel), and pre-immune serum (PIS) from the antibody-producing host failed to react with the bands (third panel). A Coomassie Brilliant Blue (CBB) stained gel of the samples showed approximately equal protein loading (lower panel). (C) An increased fraction of poorly differentiated tumors had elevated Pgrmc1 levels. Differentiation status was determined by a certified pathologist, and Pgrmc1 levels were plotted by differentiation status. The averages for each group are indicated by a horizontal line. (D-G) Immunohistochemistry for Pgrmc1 (brown staining) in the normal tissue (D) and tumor (E) in patient #4 from panel A identified strong focal staining for Pgrmc1 in the tumor as well as stainin in the adjacent non-epithelial cells. An image of panel F at higher magnifications shown in the inset.

FIG. 2 depicts Pgrmc1 expression and biological activity in SCLC cell lines. (A) Pgrmc1 expression was tested in a group of 3 commonly used SCLC cell lines (upper panel), and ku70 was used as a loading control (lower panel). (B) Pgrmc1 expression was inhibited by siRNA transfection in H226 cells, resulting in a significant loss of viability for Pgrmc1-inhibited cells (siPGR, dashed line) relative to control cells (si CON, solid line). Cells were maintained in medium lacking serum for the indicated time and in all cases, viability was determined by cell counting. (C) Pgrmc1 expression was inhibited by siRNA transfection (upper panel, lane 2) relative to the control transfection (upper panel, lane 1). (D) Adenoviruses driving the expression of a control protein (LacZ, solid line) or a heme-binding-deficient mutant of Pgrmc1 (Pgr-hbd, dashed line) demonstrated that the inactive Pgrmc1 protein inhibited H226 cell growth. Cells were maintained in media lacking serum for the indicated times. (E) The expression of the exogenous Pgrmc1-hbd protein was detected by western blot in NCI-H226 cells infected with a control adenovirus (lane 1), encoding LacZ, or the Pgrmc1-hbd expression virus (lane 2). The top panel was probed with an antibody to the HA epitope tag sequence, with which Pgrmc1-hbd is fused. (F) NCI-H226 cells were treated with increasing doses of the Pgrmc1 inhibitor AG-205 and maintained with serum (dashed line) or without serum (solid line) for 96 hours. AG-205 caused a loss of viability in the absence of serum in the SCLC cell line.

FIG. 3 depicts elevated Pgrmc1 expression in tumors of matched adenocarcinoma clinical samples. (A) Pgrmc1 expression was determined by western blot in non-malignant tissue (gray bars) and paired tumors (black bars) from the same patient. The Y-axis refers to the fold change relative to a non-malignant tissue sample that was included in each western blot. Analyses were performed in triplicate, and Pgrmc1 was significantly elevated in 6/15 samples. (B) A Pgrmc1-specific antibody recognized elevated Pgrmc1 expression in an adenocarcinoma (upper panel, lane 2) compared to matched normal tissue (upper panel, lane 1), and the reactive band was blocked by the addition of the immunogenic peptide. A Coomassie Brilliant Blue (CBB) stained gel of the samples showed approximately equal protein loading (lower panel). (C) Pgrmc1 levels correlate with survival. Adenocarcinoma patients were stratified by high and low tumor Pgrmc1 levels. Patients with lower Pgrmc1 expression had an increased overall survival (p=0.035). (D) Immunohistochemistry of Pgrmc1 (D and F) and cytokeratins (E and F) in normal (D and E) and tumor (F and G) tissue. Pgrmc1 levels were moderate in normal tissue, which contained abundant epithelial cells and was elevated in tumors, with diffuse staining compared to cytokeratins.

FIG. 4 depicts Pgrmc1 is elevated in plasma from lung cancer patients. (A) Plasma samples were partially purified by binding to Cibacron Blue columns. Pgrmc1 was analyzed by western blot of the column supernatants (upper panel), while the lower panel shows Coomassie brilliant blue staining of the samples. An equal volume was analyzed in each gel, and the sample in lane 5 was included in each gel or western blot as an internal reference. The tumor types included squamous (q), small cell (s) and adenocarcinoma (a). (B) Samples were analyzed in triplicate and plotted relative to the intensity of sample C2 (panel B; lane 5, panel A). "N" indicates normal controls, non-cancer patients, while "C" refers to cancer patients. (C) Plasma Pgrmc1 levels from 4 non-cancer patients were compared with those of patients with adenocarcinoma (adeno, N=4), squamous cell lung cancer (N=3) and large cell lung cancer (N=2), respectively, where each was measured in triplicate. Pgrmc1 levels were determined relative to sample C2 as described in panel B, above, and the average and standard deviation was calculated for each group. (D) An antibody to Pgrmc1 reacted positively in a plasma sample (top panel). Pre-immune serum from the same host animal did not react with the Pgrmc1 band (center panel), and the reactive band was blocked by the addition of immunogenic peptide (lower panel).

FIG. 5 demonstrates that Pgrmc1 is secreted by lung cancer cell lines and promotes proliferation. (A) Conditioned media from A549 cells expressing a control shRNA, lane 1, or an shRNA targeting Pgrmc1 (lane 2), were analyzed by western blot. Top panel: Pgrmc1 was readily detectable in conditioned media (lane 1) and decreased in cells in which Pgrmc1 expression was inhibited (lane 2). Lower panels: the intracellular proteins GST-P1 and ku70 were undetectable in conditioned media but abundant in cellular lysates. (B) FACS analysis of A549 control cells showed no evidence of cell death (large peak is $G_1$; right is $G_2$/M). (C) Pgrmc1 was detected by western blot in conditioned media from NCI-H226 cells. For both A and B, the conditioned medium was collected after 24 hours in serum-free medium and concentrated 10-fold prior to analysis. (D-E) Purified, recombinant Pgrmc1 was added in increasing doses to A549 NSC LC cells (D) or NCI-H226 SCLC cells (E) for 72 hours, and proliferation was measured by mean cell count (solid line) or MTT assay (dashed line). Proliferation relative to cells treated with the vehicle control is plotted on they-axis. (F) H226 SCLC cells were transfected with a plasmid encoding GFP-Pgrmc1, and cells were visualized by fluorescence microscopy (top) or bright field (bottom).

DETAILED DESCRIPTION

Pgrmc1 is induced by carcinogens in animal models, but previous studies in clinical tumor samples have been limited by the availability of key clinical endpoints. We have determined the expression of Pgrmc1 in matched lung cancer samples, and found that Pgrmc1 was elevated in 80% squamous cell lung cancers and 40% lung adenocarcinomas. In the latter disease, elevated Pgrmc1 expression correlated with overall survival, while Pgrmc1 correlated with differentiation state in the former. We have also determined the Pgrmc1 is secreted by cancer cells, albeit at lower than intracellular levels and that purified, recombinant Pgrmc1 stimulates the growth of cancer cells. Pgrmc1 is also significantly elevated in the bloodstream of the majority of cancer patients, while it was present at low levels in non-cancer control donors.

As discussed herein, Pgrmc1 expression in clinical tumor samples from squamous cell lung cancers (SCLC) and lung adenocarcinomas was analyzed compared to corresponding non-malignant tissue. Pgrmc1 expression increased significantly ($p\leq0.05$) in 12/15 SCLC samples and was elevated in poorly differentiated tumors. Pgrmc1 was highly expressed in SCLC cell lines, and SCLC cell survival was inhibited by (i) siRNA knockdown of Pgrmc1, (ii) expression of a Pgrmc1 dominant-negative mutant or (iii) the Pgrmc1 inhibitor AG-205. In adenocarcinomas, 6/15 tumors significantly over-expressed Pgrmc1, and tumor Pgrmc1 levels correlated with patient survival. Pgrmc1 localizes to secretory vesicles in cancer cells, and Pgrmc1 was secreted by lung cancer cells. In addition, elevated Pgrmc1 was detected in women with early stage lung adenocarcinoma and in large cell lung cancer compared to men (p=0.02 and 0.05, respectively). Pgrmc1 was also elevated in tumor-adjacent inflamed tissue (p=0.03, t-test). 158 head and neck tumors were analyzed and Pgrmc1 levels were found in modest but detectable amounts in normal head and neck tissue but were elevated in head and neck cancer. The Pgrmc1 levels were elevated in grade 1 versus grade 2 head and neck tumors (p=0.007, t-test), and were also elevated by stage (p=0.002, t-test). Elevated Pgrmc1 levels were also detected in neuroblastoma compared to normal peripheral nerve, and Pgrmc1 was also abundant in neuroblastoma cell lines. Kaplan-Meier plot of lung cancer patient survival (FIG. 3C) among high and low Pgrmc1-expressing tumors. Patients with tumors having lower Pgrmc1 levels had an increased overall survival (p=0.01) than those having tumors expressing higher levels of Pgrmc1. Similar results were seen in ovarian cancer but not in breast cancer, where Pgrmc1 was universally regulated and showed no correlation with survival or hormone receptors.

Figure 4:
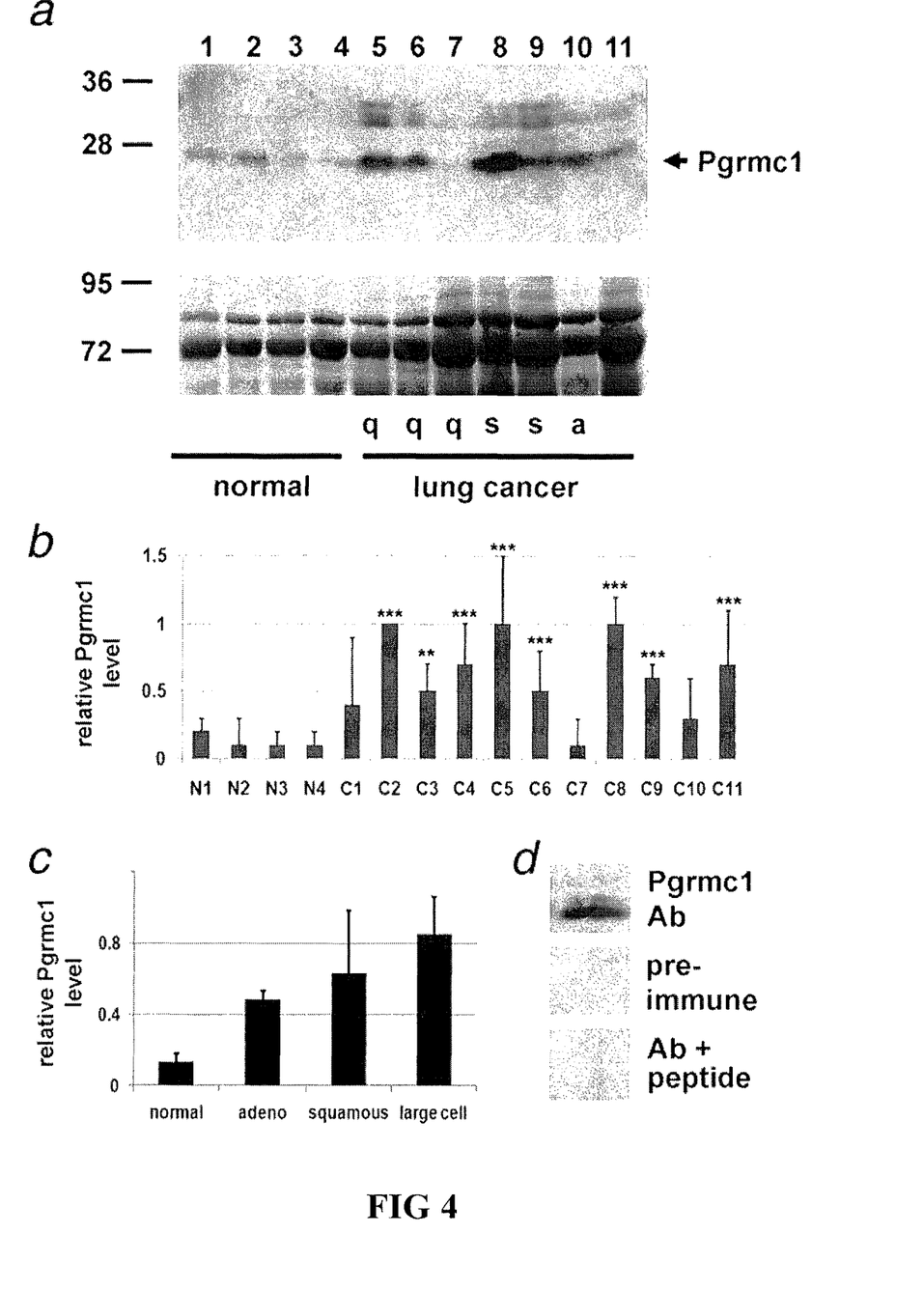

Plasma samples from subjects with lung cancer and normal controls (subjects without cancer) were analyzed and it was found that Pgrmc1 was significantly elevated in the plasma of lung cancer patients compared to non-cancer patients (FIG. 4). Together, the results demonstrate that Pgrmc1 is a serum biomarker for cancer, as well as a therapeutic target, for cancer, particularly lung cancer.

Diagnostic strategies for cancer include expensive imaging procedures that can only be performed at a few sites in the area, whereas a blood test could be performed at a distant site and a reduced cost. The levels of Pgrmc1 in bodily fluids, particularly in blood, plasma, and serum, is an effective indicator of cancer, and in accordance with the methods described here can be used to detect cancer, either alone or in combination with other biomarkers, and the levels of Pgrmc1 may be used to predict therapeutic outcome, either to Pgrmc1 inhibitors or other classes of drugs.

In the methods described herein the detection of Pgrmc1, or combinations of Pgrmc1 and other cancer biomarkers, in a bodily fluid sample, e.g., the blood, plasma or serum, of a subject is used to evaluate a subject for risk of having a cancer, e.g., a lung cancer or a head or neck cancer. The methods described herein also facilitate the identification of the stage of cancer in a subject. In the methods of this invention the cancer may be e.g., lung cancer, breast cancer, ovarian cancer, oral cancer, or head or neck cancer, in particular lung cancer, e.g., SCLC and lung adenocarcinomas, and head or neck cancer, and preferably a stage 1 lung cancer.

In the methods described herein the bodily fluid samples include blood, serum, plasma, saliva, tears or urine, or an exosome-containing fraction of such samples. Preferably the bodily fluid sample is blood, plasma, or serum, or an exosome-containing fraction thereof.

A "subject" in the context of the present invention is an animal, preferably a mammal. The mammal can be a human, non-human primate, mouse, rat, dog, cat, horse, or cow, but are not limited to these examples. In various exemplary embodiments, a subject is human and may be referred to as a patient. Mammals other than humans can be advantageously used as subjects that represent animal models of a disease or for veterinarian applications. A subject can be one who has been previously diagnosed or identified as having a cancer, and optionally has already undergone, or is undergoing, a therapeutic intervention for a cancer. Alternatively, a subject can also be one who has not been previously diagnosed as having a cancer. For example, a subject can be one who exhibits one or more risk factors for a cancer, or one who does not exhibit a cancer risk factor, or one who is asymptomatic for a cancer. A subject can also be one who is suffering from or at risk of developing a cancer. In certain embodiments, the subject can be already undergoing therapy or can be a candidate for therapy.

An aspect of this invention is a method for facilitating in the detection or diagnosis of the cancer in a subject (e.g., a human patient) comprises (a) obtaining a bodily fluid sample from a test subject, (b) determining the level of Pgrmc1 in the test subject and (c) comparing the Pgrmc1 level in the sample of the test subject to the Pgrmc1 level of a positive or negative control, wherein an elevated level of Pgrmc1 in the sample of the test subject as compared to a negative reference level is indicative of a higher risk of the test subject having a cancer. A negative reference level, or negative control, could be, e.g., the level of Pgrmc1 in a bodily fluid sample from a subject who does not have cancer, while a positive reference level, or positive control, could be, e.g., the level of Pgrmc1 in a bodily fluid sample from a subject known to have a cancer, e.g., a lung cancer. The bodily fluid sample could be, e.g., a blood, plasma or serum sample.

In accordance with the present invention, Pgrmc1 levels are "elevated" or "increased" if the levels in fluid samples of a test subject are higher than the Pgrmc1 levels in a comparable sample from a subject, or subjects, without cancer. For example, if the level of Pgrmc1 in the test sample, e.g., a blood, plasma or serum sample, is at least 2-fold, 4-fold, 6-fold, 10-fold, 15-fold, 20-fold greater, 25-fold or 30-fold greater than the level of Pgrmc1 in a comparable sample, e.g., a blood, plasma or serum sample, from a subject without a cancer then the levels of Pgrmc1 are considered to be "elevated" or "increased" and indicative of an increased risk of the test subject having a cancer, particularly a lung cancer, or a head or neck cancer. Detecting such elevated levels of Pgrmc1 facilitates the diagnosis of a subject as having a cancer and also facilitates the determination of the progression or regression of a cancer, wherein elevated levels of Pgrmc1 in samples obtained from a test subject at various times over the levels of Pgrmc1 in a subject without cancer is indicative of the progression of the cancer. In particular, a level of Pgrmc1 in a bodily fluid sample from a test subject that is at least eight-fold or at least ten fold greater than the levels found in a comparable negative control, e.g., bodily fluid sample from a subject without cancer, is indicative of an elevated risk of the test subject having a cancer, particularly a lung cancer, or a head or neck cancer. In another aspect of this invention, Pgrmc1 levels are elevated if the levels in the samples from the test subject are significantly (p<0.01) higher than the levels of Pgrmc1 in a comparable sample from a subject, or subjects, without cancer.

The methods of this invention are useful in detecting an early stage cancer wherein the cancer cells are localized and metastasis to lymph nodes or to another organ has not been detected, e.g. stage 1 lung cancer, or a late stage cancer where in the cancer has metastasized and is found in the lymph nodes or in more than one organ. The methods of this invention are particularly useful in detecting early stage cancers, e.g. stage 1 lung cancer. In an aspect of this invention, if the level of Pgrmc1 in the test sample is about ten-fold or at least ten fold greater than the levels found in a comparable negative control sample, such elevated levels are indicative of an elevated risk of the test subject having an early stage cancer, particularly an early stage lung cancer, e.g., stage 1 lung cancer.

An aspect of this invention is a method for facilitating the screening or diagnosis of a subject for cancer. The method comprises the steps of: obtaining a body fluid from the subject; and measuring the secreted Pgrmc1 levels in the bodily fluid to facilitate the screening or diagnosis of the subject for cancer. For example, the method comprises the steps of: a) isolating or obtaining a bodily fluid sample, e.g., blood, plasma or serum, from a subject to be tested (i.e., "test sample"); b) determining the levels of Pgrmc1 in the test sample, c) comparing the levels of Pgrmc1 in the test sample to the levels of Pgrmc1 in a reference sample, wherein an increase or decrease in Pgrmc1 levels over the level in the reference sample is indicative of the cancer. The subject to be tested may be, e.g., an individual suspected of having, or who has a cancer, e.g., a lung cancer. In certain embodiments, the Pgrmc1 level in the reference sample may be the level in samples collected from the test subject or from a different subject. For example, a baseline Pgrmc1 level can be determined from an analysis of samples from the same subject at different time points. Alternatively, the Pgrmc1 level in a reference sample could be the level obtained based on the analysis of samples taken from control subjects sharing one or more of gender, age, or weight with the test subject. The bodily fluid samples may be, e.g., blood, serum, plasma, saliva, tears or urine or an exosome-containing fraction thereof. Preferably the biological fluid sample is blood, plasma, or serum, or an exosome-containing fraction thereof. The reference sample may be a negative reference sample, or negative control sample, wherein the sample is from a subject who does not have cancer. Alternatively the reference sample may be a positive reference sample, or a positive control sample, wherein the sample is from a subject who has a cancer, preferably the type of cancer that test subject is suspected of having.

In the methods described herein the cancer is detected when the secreted Pgrmc1 level in the body fluid is increased relative to the secreted Pgrmc1 level in the sample from the reference, or control, sample. A negative reference sample may be, e.g., a body fluid of an individual without cancer or the negative reference sample may be, e.g., the average levels of Pgrmc1 derived from population studies on subjects who did not develop cancer.

In methods wherein the reference sample is a negative reference sample, the cancer is detected when the secreted Pgrmc1 level in the body fluid is increased relative to the secreted Pgrmc1 level in the body fluid of a subject without cancer. In methods wherein the reference sample is a positive reference sample, the cancer is detected when the secreted Pgrmc1 levels are higher than of not significantly different then the levels in the positive reference sample.

Also an aspect of this invention is a method of detecting the presence of a cancer in an individual, wherein the individual is suspected of having, or has a cancer, said method comprising: a) contacting a test bodily fluid sample from the individual with an antibody that specifically binds to Pgrmc1; b) detecting the level of Pgrmc1 in the test sample that specifically binds the antibody; and, c) comparing the level of Pgrmc1 in the test sample to the level of Pgrmc1 that specifically binds the antibody in a corresponding normal bodily fluid sample; wherein an elevated level of Pgrmc1 in the test sample relative to the normal sample is an indication of the presence of the cancer in the individual. A normal bodily fluid sample is a bodily fluid sample from an individual who does not have cancer. If the antibody binds to other proteins in the samples in addition to Pgrmc1, alternatively, the level of protein binding to the antibody in the samples may be compared and an elevated level of protein binding the antibody in the test sample relative to the level of protein binding the antibody the normal sample is an indication of the presence of the cancer in the individual.

The invention described herein also includes methods for monitoring the progression or regression of cancer in a patient who has a cancer, by: a) contacting a first bodily fluid sample from the patient with an antibody that specifically binds Pgrmc1 and quantitatively determining the level of protein in the sample that specifically binds the antibody; b) contacting a second bodily fluid sample from the patient with an antibody that specifically binds Pgrmc1 and quantitatively determining the level of Pgrmc1 in the sample that specifically binds the antibody, wherein the second sample is obtained at a period of time after the first sample is obtained; and c) comparing the level of Pgrmc1 bound to the antibody in the first sample to the level of Pgrmc1 bound to the antibody in the second sample, wherein a difference in the levels is indicative of the progression or regression of the cancer, wherein increasing levels of Pgrmc1 is indicative of a progressing cancer. If the antibody binds to other proteins in the samples in addition to Pgrmc1, the level of protein binding to the antibody in the samples may be compared and an elevated level of protein binding the antibody in the test sample relative to the level of protein binding the antibody the normal sample is an indication of the presence of the cancer in the individual. The test subject may be, e.g., a subject who has received one or more therapeutic treatments for a cancer.

Another aspect of this invention is a method for assessing the risk of a subject for having cancer, comprising: detecting the level of a Pgrmc1 in a sample from test subject and comparing the detected level with a reference level, wherein a level in the sample of the test subject below the reference level is indicative of a lower risk of the test subject having cancer; and wherein a level in the sample of the test subject above the reference level is indicative of a higher risk of the test subject having cancer.

The antibodies useful in the methods of this invention include polyclonal antibodies and monoclonal antibodies that bind Pgrmc1. The antibodies may bind specifically to a denatured form of Pgrmc1 or may bind to the nondenatured form of Pgrmc1 or both. Preferably, the antibody binds to the nondenatured form of Pgrmc1. Antibodies that bind to Pgrmc1 are well-known in the art and are commercially available.

As used herein, the term "antibody" means a protein comprising one or more polypeptides substantially encoded by all or part of the recognized immunoglobulin genes. The recognized immunoglobulin genes, for example in humans, include the kappa ($\kappa$), lambda ($\lambda$) and heavy chain genetic loci, which together compose the myriad variable region genes, and the constant region genes mu ($\mu$), delta ($\delta$), gamma ($\gamma$), epsilon ($\epsilon$) and alpha ($\alpha$), which encode the IgM, IgD, IgG, IgE, and IgA isotypes respectively. Antibody herein is meant to include full length antibodies and antibody fragments, and may refer to a natural antibody from any organism, an engineered antibody or an antibody generated recombinantly for experimental, therapeutic or other purposes as further defined below. Antibody fragments include Fab, Fab', F(ab')$_2$, Fv, scFv or other antigen-binding subsequences of antibodies and can include those produced by the modification of whole antibodies or those synthesized de novo using recombinant DNA technologies. The term "antibody" refers to both monoclonal and polyclonal antibodies. Antibodies can be antagonists, agonists, neutralizing, inhibitory or stimulatory.

The bodily fluid sample to be assayed for levels of Pgrmc1 in the methods of this invention may be from any subject, e.g., a subject having a cancer or suspected of having a cancer, a subject who smokes, a subject who has a family history of cancer, e.g., lung cancer or a head or neck cancer, a subject who is exposed to carcinogenic agents, or a subject having a chronic cough.

The level of Pgrmc1 in a bodily fluid may be detected by a variety of methods, e.g., immunoassays. Immunoassays carried out in accordance with the present invention may be homogeneous assays or heterogeneous assays and may be used for the qualitative and/or the quantitative assessment of Pgrmc1 in a bodily sample. In a homogeneous assay the immunological reaction usually involves the specific antibody (e.g., anti-Pgrmc1 protein antibody), a labeled analyte, and the sample of interest. The signal arising from the label is modified, directly or indirectly, upon the binding of the antibody to the labeled analyte. Both the immunological reaction and detection of the extent thereof can be carried out in a homogeneous solution. Immunochemical labels which may be employed include free radicals, radioisotopes, fluorescent dyes, enzymes, bacteriophages, or coenzymes.

In a heterogeneous assay approach, the reagents are usually the sample, the antibody, and means for producing a detectable signal. Samples as described above may be used. The antibody can be immobilized on a support, such as a bead (such as protein A and protein G agarose beads), plate or slide, and contacted with the specimen suspected of containing the antigen in a liquid phase. The support is then separated from the liquid phase and either the support phase or the liquid phase is examined for a detectable signal employing means for producing such signal. The signal is related to the presence of the analyte in the sample. Means for producing a detectable signal include the use of radioactive labels, fluorescent labels, or enzyme labels. For example, if the antigen to be detected contains a second binding site, an antibody which binds to that site can be conjugated to a detectable group and added to the liquid phase reaction solution before the separation step. The presence of the detectable group on the solid support indicates the presence of the antigen in the test sample. Examples of suitable immunoassays include, but are not limited to oligonucleotides, immunoblotting, immunoprecipitation, immunofluorescence methods, chemiluminescence methods, electrochemiluminescence (ECL) or enzyme-linked immunoassays.

Those skilled in the art will be familiar with numerous specific immunoassay formats and variations thereof which may be useful for carrying out the method disclosed herein. See generally E. Maggio, Enzyme-Immunoassay, (1980) (CRC Press, Inc., Boca Raton, Fla.); see also U.S. Pat. No. 4,727,022 to Skold et al., titled "Methods for Modulating Ligand-Receptor Interactions and their Application," U.S. Pat. No. 4,659,678 to Forrest et al., titled "Immunoassay of Antigens," U.S. Pat. No. 4,376,110 to David et al., titled "Immunometric Assays Using Monoclonal Antibodies," U.S. Pat. No. 4,275,149 to Litman et al., titled "Macromolecular Environment Control in Specific Receptor Assays," U.S. Pat. No. 4,233,402 to Maggio et al., titled "Reagents and Method Employing Channeling," and U.S. Pat. No. 4,230,797 to Boguslaski et al., titled "Heterogeneous Specific Binding Assay Employing a Coenzyme as Label."

Antibodies can be conjugated to a solid support suitable for a diagnostic assay (e.g., beads such as protein A or protein G agarose, microspheres, plates, slides or wells formed from materials such as latex or polystyrene) in accordance with known techniques, such as passive binding. Antibodies as described herein may likewise be conjugated to detectable labels or groups such as radiolabels (e.g., $S^{35}$, $I^{125}$, $I^{131}$)luminescent and enzyme labels (e.g., horseradish peroxidase, alkaline phosphatase, luciferase), and fluorescent labels (e.g., fluorescein, green fluorescent protein, rhodamine) in accordance with known techniques.

Antibodies can also be useful for detecting post-translational modifications of Pgrmc1 proteins, polypeptides, mutations, and polymorphisms, such as tyrosine phosphorylation, threonine phosphorylation, serine phosphorylation, glycosylation (e.g., O-GlcNAc). Such antibodies specifically detect the phosphorylated amino acids in a protein or proteins of interest, and can be used in immunoblotting, immunofluorescence, and ELISA assays. These antibodies are well-known to those skilled in the art, and commercially available. Post-translational modifications can also be determined using metastable ions in reflector matrix-assisted laser desorption ionization-time of flight mass spectrometry (MALDI-TOF) (Wirth et al., (2002) Proteomics 2(10): 1445-51).

In another aspect of the invention, the detection of Pgrmc1 to facilitate in the diagnosis of cancer status entails contacting a sample from a subject with a substrate, e.g., a SELDI probe, having an adsorbent thereon, under conditions that allow binding between the Pgrmc1 and the adsorbent, and then detecting the Pgrmc1 bound to the adsorbent by gas phase ion spectrometry, for example, mass spectrometry. Other detection paradigms that can be employed to this end include optical methods, electrochemical methods (voltametry and amperometry techniques), atomic force microscopy, and radio frequency methods, e.g., multipolar resonance spectroscopy. Illustrative of optical methods, in addition to microscopy, both confocal and non-confocal, are detection of fluorescence, luminescence, chemiluminescence, absorbance, reflectance, transmittance, and birefringence or refractive index (e.g., surface plasmon resonance, ellipsometry, a resonant mirror method, a grating coupler waveguide method or interferometry).

Software used to analyze the data can include code that applies an algorithm to the analysis of the signal to determine whether the signal represents a peak in a signal that corresponds to a biomarker according to the present invention. The software also can subject the data regarding observed biomarker peaks to classification tree or ANN analysis, to determine whether a biomarker peak or combination of biomarker peaks is present that indicates lung cancer status. Analysis of the data may be "keyed" to a variety of parameters that are obtained either directly or indirectly from the mass spectrometric analysis of the sample. These parameters include, but are not limited to, the presence or absence of one or more peaks, the height of one or more peaks, the log of the height of one or more peaks, and other arithmetic manipulations of peak height data.

In an embodiment of this invention, the detection of secreted Pgrmc1 for diagnosis of cancer in a subject entails contacting a sample from a subject or patient, preferably a blood, plasma or serum sample, with a substrate having an adsorbent thereon under conditions that allow binding between the secreted Pgrmc1 and the adsorbent, and then detecting the secreted Pgrmc1 bound to the adsorbent by gas phase ion spectrometry, preferably by Surface Enhanced Laser Desorption/Ionization (SELDI) mass spectrometry.

The detection of the secreted Pgrmc1 can he enhanced by using certain selectivity conditions, e.g., adsorbents or washing solutions, or by functionalizing the absorbent with e.g. an antibody that specifically binds Pgrmc1. However, other adsorbents can be used, as long as they have the binding characteristics suitable for binding Pgrmc1.

More particularly, armed with the information regarding Pgrmc1, various methods can be used to recognize patterns of doublets, triplets, and higher combinations of biomarkers according to the invention. These methods take raw data regarding which peaks are present and their intensity and provide a differential diagnosis of lung cancer versus normal for a sample.

Thus, the process can be divided into the learning phase and the classification phase. In the learning phase, a learning algorithm is applied to a data set that includes members of the different classes that are meant to be classified, for example, data from a plurality of samples diagnosed as cancer and data from a plurality of samples assigned a negative diagnosis. The methods used to analyze the data include, but are not limited to, artificial neural network, support vector machines, genetic algorithm and self-organizing maps and classification and regression tree analysis. These methods are described, for example, in WO 01/31579, May 3, 2001 (Barnhill et al.); WO 02/06829, Jan. 24, 2002 (Hitt et al.) and WO 02/42733, May 30, 2002 (Paulse et al.). The learning algorithm produces a classifying algorithm. The classifier is keyed to elements of the data, such as particular markers and particular intensities of markers, usually in combination, that can classify an unknown sample into one of the two classes. The classifier is ultimately used for diagnostic testing.

Software, both freeware and proprietary software, is readily available to analyze such patterns in data, and to devise additional patterns with any predetermined criteria for success. Those biomarkers which by themselves are predictive of a differential diagnosis of lung cancer versus normal do not require pattern recognition software to analyze the data.

In another aspect, the present invention provides kits for facilitating the diagnosis of cancer status, which kits are used to detect secreted Pgrmc1 levels according to the invention. The kits screen for the presence of secreted Pgrmc1, or secreted Pgrmc1 and combinations of other biomarkers that are differentially present in samples from normal subjects and subjects with cancer.

The kits of this invention are useful for facilitating the detection of, or diagnosis or prognosis of a cancer by detecting Pgrmc1, or Pgrmc1 and one or more biomarkers for a cancer, in a bodily fluid. The kit comprises biomarker detecting reagents for detecting the Pgrmc1 and the one or more biomarkers, and instructions for using the reagents to detect the biomarkers from the bodily fluids and facilitating the diagnosis or prognosis of the cancer. As used herein, the term "biomarker detecting reagents" refers to any substances, antibodies, receptors, chemicals, solutions used in reactions and processes that are capable of detecting, measuring, and examining Pgrmc1 and any additional biomarkers and their isoforms of interest. In one embodiments, the cancer is lung cancer or head or neck cancer and the biomarker is Pgrmc1. In other preferred embodiments, the biomarker detecting reagents used herein comprise antibodies that specifically bind to Pgrmc1, e.g. a polyclonal or monoclonal antibody that was raised against a Pgrmc1 immunogenic fragment. For example, the kits may comprise a first monoclonal or polyclonal antibody raised against a peptide of Pgrmc1, e.g., the peptide having the amino acid sequence QPAASGDSDDDE (SEQ ID NO:1). The kits of this invention may comprise a second monoclonal or polyclonal, wherein the second antibody binds to the first antibody. The antibodies may be antibodies coupled to a detectable substance, which facilitates their detection. Examples of detectable substances include various enzymes, prosthetic groups, fluorescent materials, luminescent materials, bioluminescent materials, radioactive materials, positron emitting metals using various positron emission tomographies, and nonradioactive paramagnetic metal ions. See, for example, U.S. Pat. No. 4,741,900 for metal ions which can be conjugated to antibodies for use in the present invention. Examples of suitable enzymes include horseradish peroxidase, alkaline phosphatase, beta-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material include $I^{125}$, $I^{131}$, $I^{111}$ or $TC^{99}$. Ligands that bind to Pgrmc1 and monoclonal and polyclonal antibodies that bind Pgrmc1, e.g., monoclonal and polyclonal antibodies raised against Pgrmc1 peptides, e.g., a peptide consisting of or comprising SEQ ID NO: 1, including labeled or unlabelled binding ligands and antibodies may also be used to detect Pgrmc1 in the methods of this invention.

The kit of the present invention further comprises an instruction for use in aiding in diagnosing, monitoring progression of, or in the prognosis of, breast cancer. In an embodiment, the instruction provides that an elevated Pgrmc1 level in a bodily fluid or in isolated exosomes as compared to a negative control, e.g., the level of Pgrmc1 in the comparable bodily fluid or isolated exosomes from subject known not to have cancer, indicates an association with cancer. In yet another embodiment, the instruction in the kit instructs the isolation of the bodily fluid or exosome containing fraction of the bodily fluid from a subject at various intervals, e.g., weekly, monthly, biannually, annually etc, and the measurement and comparison of Pgrmc1 levels in the bodily fluid or exosome containing fraction using the detection reagents in the kit. An increasing level of Pgrmc1 in the samples over time is associated with progression of a cancer, wherein a decreasing level of Pgrmc1 in the samples over time is associated with regression of a cancer.

The instructions in the kits of this invention may be present in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another means would be a computer readable medium, e.g., diskette, CD, etc., on which the information has been recorded. Yet another form that may be present is a website address which may be used via the internet to access the information at a removed site. Any convenient form may be present in the kits.

The kits may also comprise a computer or a component of a computer, such as a computer-readable storage medium or device. Examples of storage media include, without limitation, optical disks such as CD, DVD and Blu-ray Discs (BD); magneto-optical disks; magnetic media such as magnetic tape and internal hard disks and removable disks; semi-conductor memory devices such as EPROM, EEPROM and flash memory; and RAM. The computer-readable storage medium may comprise software encoding references to the various therapies and treatment regimens disclosed herein. The software may be interpreted by a computer to provide the practitioner with treatments according to various measured concentrations of Pgrmc1 as provided herein. In various embodiments, the kit comprises a biomarker assay involving a lateral-flow-based point-of-care rapid test with detection of risk thresholds, or a biochip with quantitative assays for Pgrmc1.

The following examples are offered by way of illustration, and are not limiting.

EXAMPLE 1

Figure 1:
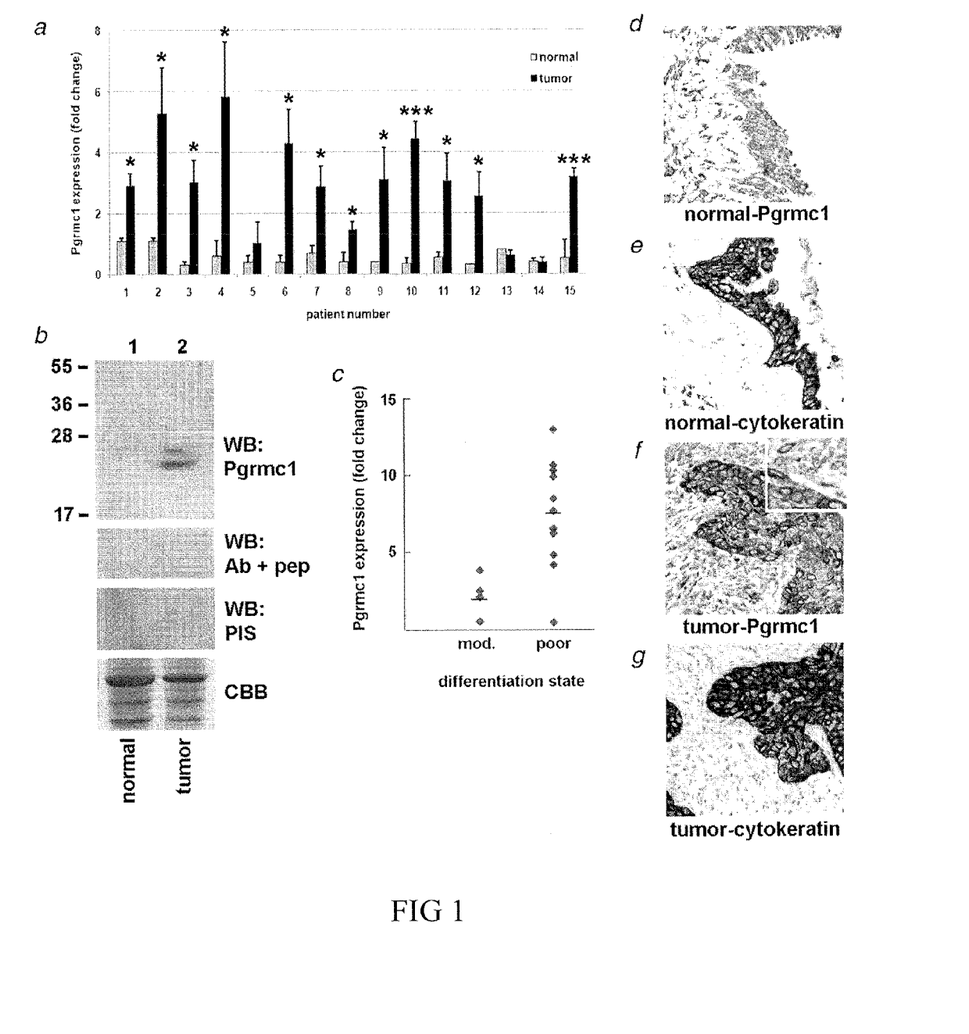

Pgrmc1 Levels Correlate with Differentiation Status in Squamous Cell Lung Carcinoma In 15 matched samples of SCLC with adjacent nonmalignant tissue, Pgrmc1 was overexpressed significantly in 12/15 of the tumors relative to nonmalignant tissue from the same patient as determined by western blot in nonmalignant tissue (gray bars) and paired tumors (black bars) from the same patient. (FIG. 1A). Samples 5, 13 and 14 were the exceptions (FIG. 1A). A Pgrmc1-specific antibody recognized elevated Pgrmc1 levels in an SCLC tumor (FIG. 1B, upper panel, lane 2) compared to matched normal tissue (FIG. 1B, upper panel, lane 1). Pgrmc1 recognized a band of 25 kDa in nonmalignant tissue and a doublet of bands in the majority of tumors, and both bands were blocked by the immunogenic peptide, while neither band was recognized by preimmune serum (PIS) (FIG. 1B). Samples were analyzed in triplicate, and overall Pgrmc1 levels relative to the matched nonmalignant tissue ranged from 0.7-fold to 13-fold (FIG. 1A, Samples 13 and 10, respectively). The increase in Pgrmc1 was significant (p=0.01-0.05 for tumors 1-4, 6-9 and 11-12, while p=0.002 for tumor #10 and 0.005 for #15, t-test). Thus, Pgrmc1 levels were elevated in 80% of SCLC relative to adjacent nonmalignant tissue from the same patient. There was little change between nonmalignant tissues in different patients (FIG. 1A). Among the tumors in which Pgrmc1 was induced by >5-fold relative to the adjacent nonmalignant tissue, 8/8 were poorly differentiated (FIG. 1C, right column). In contrast, among the tumors with <4-fold Pgrmc1 induction, 4/7 were moderately differentiated. In the entire set of tumors, Pgrmc1 levels correlated significantly with poor differentiation state (p=0.02, t-test). In contrast, Pgrmc1 levels did not correlate with age at diagnosis or gender. As expected from the western blot analysis, immunohistochemistry revealed moderate staining in the normal tissue from Patient 4 (FIG. 1D) and strong staining in the adjacent tumor (FIG. 1F). A higher magnification of the staining is shown as an inset for FIG. 1F and demonstrated cytoplasmic staining. Cytokeratin staining of the same samples revealed abundant epithelial cells in the normal tissue (FIG. 1E) and areas of concentrated epithelial cells in the tumor tissue (FIG. 1G). Quantitation of three separate cytokeratin-positive areas for Pgrmc1 staining demonstrated 2.3-fold higher Pgrmc1 staining in the tumor epithelial cells compared to the same area of epithelial adjacent normal tissue (p=0.002, t-test). Notably, Pgrmc1 was expressed in epithelial tumor cells as well as nonepithelial adjacent cells (FIG. 1F), suggesting a potential role for Pgrmc1 in nonepithelial cells within tumors.

EXAMPLE 2

Pgrmc1 Increases Viability in Squamous Lung Cancer Cell Lines

Figure 2:
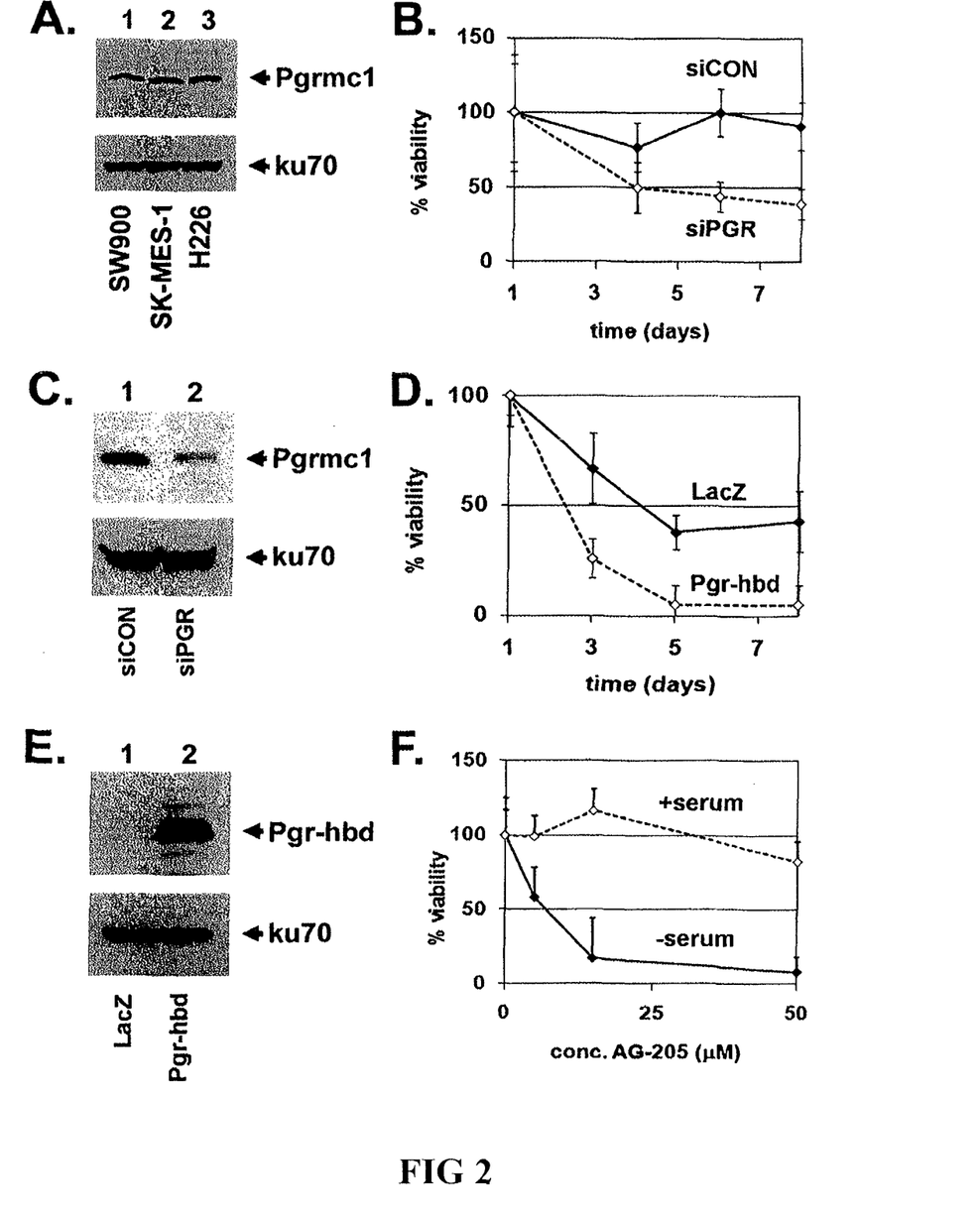

Pgrmc1 expression had not been characterized in squamous cell cancers previously, and Pgrmc1 was readily detectable in SW900, SKMES-1 and NCI-H226 cells (FIG. 2A). Pgrmc1 inhibition by RNA inhibition (RNAi) suppressed proliferation in the non-small cell lung cancer (NSCLC) adenocarcinoma cell line A549 but had little effect on cell survival (Ahmed et al., J Pharmacal Exp Ther 2010; 333:564-73). In contrast, RNAi of Pgrmc1 in NCI-H226 cells decreased the cell number (FIG. 2B), and the knockdown of Pgrmc1 expression was verified by western blot (FIG. 2C). Loss of viability after siRNA transfection was not through the apoptotic pathway, because the cleavage of caspase 3 and caspase 8 were unaffected (FIG. 1A) and etoposide treatment served as a positive control for apoptosis (FIG. 1B).

Therapeutic options for SCLC are limited. However, a recently characterized Pgrmc1 inhibitor, AG-205, efficiently inhibited the growth of NCI-H226 cells (FIG. 2F). The compound was most active in the absence of serum (FIG. 2F, solid line), where it had an $IC_{50}$ of 9 μM. In the presence of serum, the compound had minimal activity (FIG. 2F, dashed line). Thus, Pgrmc1 is expressed in cultured SCLC cell lines, where it promotes cell survival, and this activity is suppressed by a Pgrmc1 small molecule inhibitor.

EXAMPLE 3

Pgrmc1 Levels Correlate with Survival in Lung Adenocarcinomas

Figure 3:
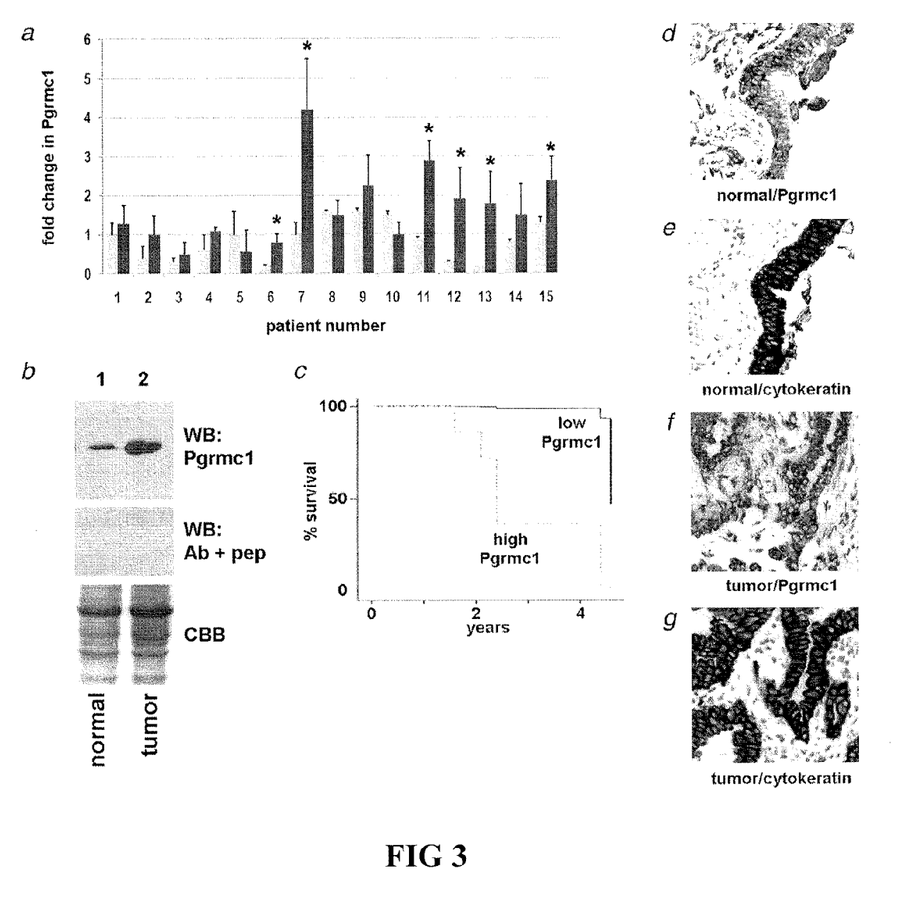

Pgrmc1 promotes tumor formation and metastatic spread in adenocarcinoma cell lines. In a panel of 15 paired sets of lung adenocarcinomas with nonmalignant tissue from the same patient, Pgrmc1 was significantly elevated in 6/15 adenocarcinomas. Pgrmc1 levels varied more in nonmalignant tissue adjacent to the tumors than for squamous cell carcinomas (FIG. 3A). Similar to the SCLC analysis, the band recognized by the Pgrmc1 antibody was blocked by the addition of immunogenic peptide (FIG. 3B, Patient 7 from FIG. 3A).

To determine the clinical impact of Pgrmc1 levels, tumors were grouped by low or high Pgrmc1 tumor levels, and Pgrmc1 levels correlated inversely with survival in the patients (FIG. 3C, p=0.035). There was a trend between survival and Pgrmc1 levels in the nonmalignant tissues adjacent to the tumors that did not achieve significance. In contrast to SCLC, Pgrmc1 levels did not correlate to a significant extent with differentiation status in this cohort of lung adenocarcinomas. As for squamous cell cancers (FIG. 1), Pgrmc1 was moderately expressed in tumor-adjacent normal lung tissue (FIG. 3D) and was detected in nonepithelial cells adjacent to cytokeratin-positive lung tumor cells (FIGS. 3F and 3G). Cytokeratin staining revealed abundant epithelial cells in the nontumor tissue (FIG. 3E). Quantitation of three separate cytokeratin-positive areas for Pgrmc1 staining revealed 1.5-fold higher Pgrmc1 staining in the adenocarcinoma epithelial cells compared to the same area of epithelial adjacent normal tissue (p=0.03, t-test).

EXAMPLE 4

Pgrmc1 Detection in Plasma from Lung Cancer Patients

We detected Pgrmc1/sigma2 receptor in endosomes within cancer cells and demonstrated the movement of Pgrmc1/sigma2 receptor moving within cancer cells and could see it secreted (data not show). We purified plasma and the exosome fractions of plasma from lung cancer patients, and cancer free subjects by using well known methods in the art. We detected Pgrmc1 in exosomes, and surprisingly also in unfractionated plasma, in both cancer patients and normal subjects. Met and PKM2 were used as markers for exosomes (Kimura et al. J Bioi Chern 2008; 283:4323-31; Kimura et al., J Neurochem 2010; 112:1156-67). Because exosomes require a lengthy purification process, most analysis were conducted with plasma.

Pgrmc1 was present in low but detectable levels in plasma of cancer free individuals (FIG. 4A, lanes 1-4). In contrast, Pgrmc1 levels were significantly elevated in the plasma of 8/11 lung cancer patients (FIGS. 4A, lanes 5-11 and 4B), including patients with adenocarcinoma, squamous cell carcinoma and large cell cancers (FIG. 4C). The Pgrmc1 band was not detected with preimmune serum from the animal in which the anti-Pgrmc1 antibody was raised (FIG. 4D, center) or after addition of the immunogenic peptide (FIG. 4D, lower panel).

EXAMPLE 5

Figure 5:
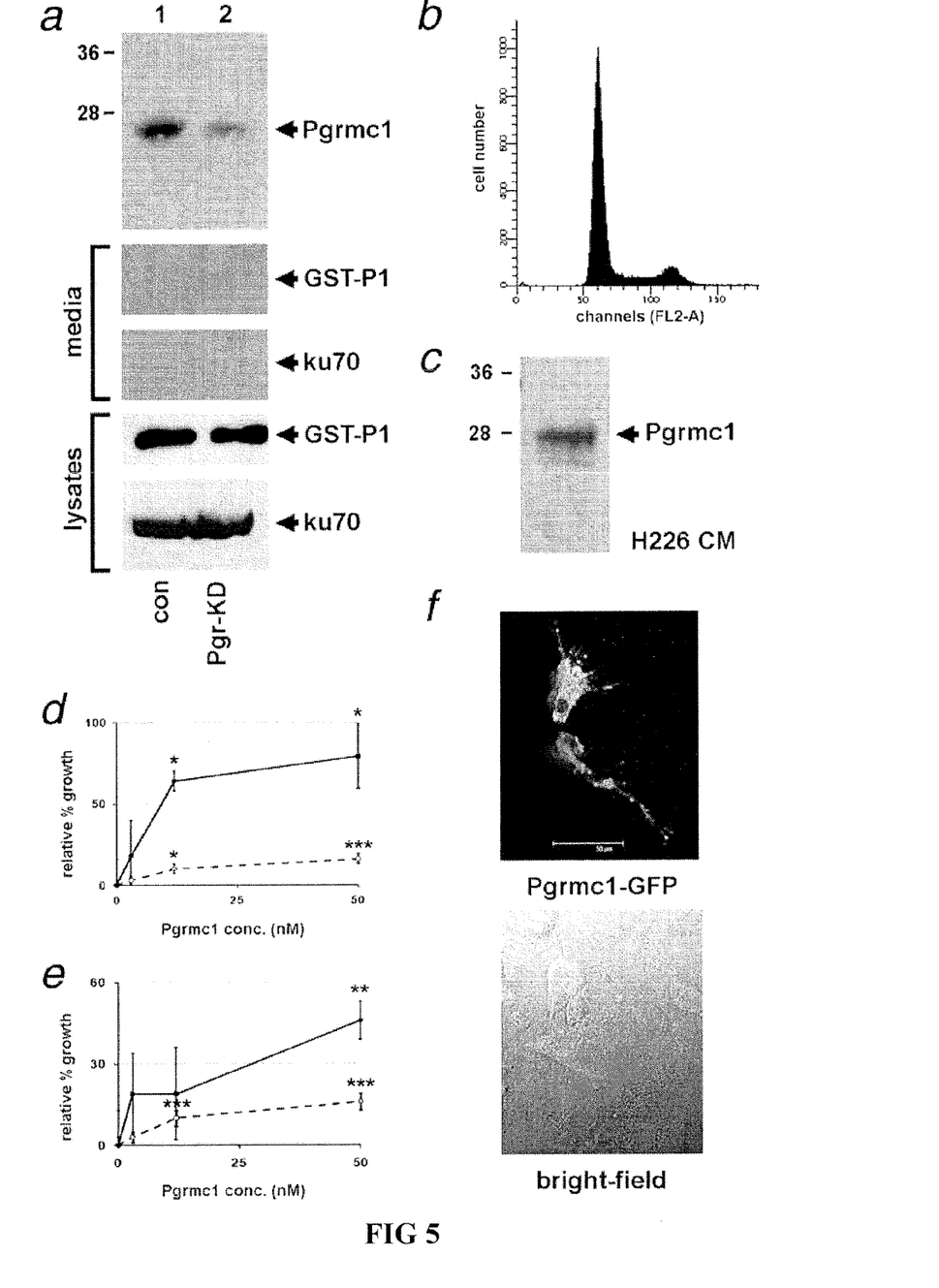
Figure 6:
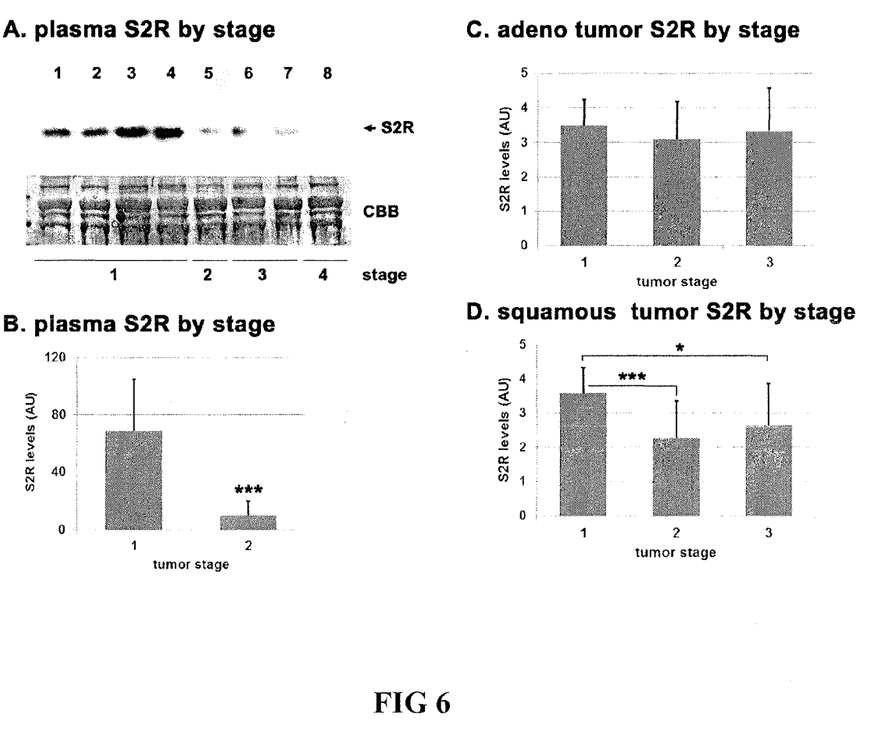
FIG. 6 depicts Pgrmc1 expression in plasma and tumors by stage. (A) Western blot of plasma Pgrmc1 levels in stage 1-4 lung tumors. Samples were prepared and analyzed using the protocol described in FIG. 4. The lower panel shows a loading control—the same samples separated by SDS-PAGE and stained with Coomassie Brilliant Blue. (B) Quantitation of the results from part A. Stage 1 tumors had significantly higher plasma Pgrmc1 levels than those of patients with stage 2, 3 and 4 tumors. (C) Immunohistochemistry of stage 1 (n=10), stage 2 (n=10) and stage 3 (n=12) lung adenocarcinomas showing no significant increase with tumor stage. (D) Immunohistochemistry of stage 1 (n=12), stage 2 (n=13) and stage 3 (n=29) squamous cell lung carcinomas, showing a significant decrease in Pgrmc1 staining from stage 1 to stage 2 tumors that remained in stage 3 tumors. Stage 2 and 3 tumors were not significantly different. We conclude that Pgrmc1 levels in plasma are significantly higher in early stage lung tumors. This difference may reflect differences in Pgrmc1 secretion during the development of lung cancer.

Secretion Of Pgrmc1 by Tumor Cell Lines and Effects of Pgrmc1 on Tumor Cell Proliferation To address the potential source of plasma Pgrmc1, we compared conditioned media from control or Pgrmc1 knockdown cells expressing a short hairpin RNA targeting Pgrmc1. Pgrmc1 was abundant in media from the control cell line (FIG. 5A, top, lane 1) but attenuated in the knockdown cell line (FIG. 5A, top, lane 2). It is unlikely that Pgrmc1 could be released from dead cells in the population because the cells were primarily arrested in G1, with no evidence of sub-G1 content (FIG. 5B) or cell death under the conditions used for harvest (24 hr in no serum), and we were unable to detect the intracellular proteins GST-P1 and ku70 in conditioned media (FIG. 5A, media), even though they were abundant within the cells (FIG. 5A, lysates). Pgrmc1 was also readily detectable in the conditioned media of an SCLC cell line, H226 (FIG. 5C). Secreted Neudesin/NENF (neuron-derived neurotrophic factor) and neuferricin stimulate growth in neurons (Kimura et al., J Neurosci Res 2005, 79:287-94; Kimura et al., J Biol Chem 2008, 283:4323-31; Kimura et al., J Neurochem 2010,112:1156-67) and we found that purified, recombinant Pgrmc1 had a similar activity towards A549 (FIG. 5D) and H226 (FIG. 5E) cells. Viability was measured by two different assays—mean cell count and MTT assays (FIGS. 5D-5E, solid and dashed lines, respectively).

The localization of Pgrmc1 is highly variable in different cell types, with the protein localizing to the endoplasmic reticulum or secretory apparatus, plasma membrane and nucleus in various cell types (Nolte et al., Biochim Biophys Acta 2000, 1543:123-30; Min et al., FEBS J 2005, 272: 5832-43; Marek et al., Comp Hepatol 2009, 8:1; Roy et al., Biochim Biophys Acta 2010,1804:1869-81; Ahmed J Biol Chem 2010; Peluso et al., Endocrinology 2006, 147:3133-40; Krebs et al., Proc Natl Acad Sci USA 2000, 97:12816-21; Shin et al., J Biol Chem 2003, 278:7607-16; Labombarda et al., J Neurochem 2003; 87:902-13). To determine the localization of Pgrmc1 in squamous cell cancers, we transfected NCI-H226 cells with plasmids encoding green fluorescent protein (GFP) or GFP fused to Pgrmc1. Pgrmc1 localized to punctate sites within the cytoplasm with minimal nuclear staining (FIG. 5F and FIG. 1).

Materials and Methods

Tumor samples: All non-malignant and tumor solid tissue samples were obtained from the University of Kentucky Biospecimen Core Program, and serum samples were obtained directly from the Markey Cancer Center. All protocols were approved by the Institutional Review Board. The clinical characteristics of the patients donating solid tumors are described in Table I. Tumor tissues and non-cancerous alveolar epithelial tissues from peripheral portions of the lung resection were collected based on gross characteristics (texture and color) with confirmed histological analysis. Non-cancerous tissues in the study were selected by the absence of neoplastic changes in the tissue, based on evaluation by the Director of the Tissue Procurement Facility, an Anatomic Pathology/Clinical Pathology board-certified pathologist. Tumors were classified as well, moderately or poorly differentiated by a certified pathologist (Table I).

Immunohistochemistry was performed at the University of Kentucky Histology Laboratory with the Dako Envision kit (Dako, Carpinteria, Calif.), blocking in 3% bovine serum albumin and probing with an anti-Pgrmc1 antibody (ProteinTech Group, Chicago, Ill.). Sections from the same region of the normal or tumor tissue were imaged. Quantitation was with Adobe Photoshop and ImageJ software, analyzing median pixel density in three nonadjacent, cytokeratinpositive sections of the same samples.

Western blotting: Tumor samples were disrupted in radioimmunoprecipitation (RIPA) buffer using a polytron P3000 homogenizer on ice. Samples were centrifuged at 13,000×g for 10 minutes at 4° C, and the protein concentrations of the supernatants were measured by BCA assay. 100 µg of each lysate was analyzed by western blot using the antibodies PGR-UK1 (anti-Pgrmc1, raised to amino acids 49-60, C-terminal to the putative membrane spanning sequence; Ahmed et al., J Pharmacol Exp Ther 2010; 333: 564-73), anti-caspase 3 (Santa Cruz Biotechnologies, Santa Cruz, Calif.), anti-caspase 8 (Santa Cruz), anti-cytokeratin cocktail (AE1/AE3, Dako), anti-ku70 (Santa Cruz), anti-HA11 (BAbCo, Richmond, Calif.) and anti-glutathione S-transferase (GST)-P1 (Genscript, Piscataway, N.J.). Peptide blocking experiments were performed using an equimolar amount of immunogenic peptide (amino acids 49-60 of Pgrmc1). Each sample of non-malignant tissue and adjacent tumor was analyzed in three separate western blots, using a reference protein sample (non-malignant tissue of adenocarcinoma patient #229) on each blot. All SDS-PAGE gels contained 10% acrylamide. The same tumors were analyzed by SDS-PAGE and stained with Coomassie Brilliant Blue. Three bands which were present in all of the samples were scanned and the sum of the bands was used to derive the loading control. Pgrmc1 bands were quantitated using Adobe Photoshop and divided by the intensity of the reference band and loading controls. For the survival analysis, tumors were grouped into low Pgrmc1 (≤1 relative to the normal control) or high Pgrmc1 (>1) and analyzed by Cox regression analysis.

For blood samples, plasma was centrifuged at 13,000×g for 10 minutes, and the supernatant was diluted 1:1 in 20 mM Tris, pH 7.4 and incubated with 200 µl of Separopore blue CL-6B (Bio-world, Dublin, Ohio) slurry (equilibrated in 20 mM Tris, pH 7.4) for 30 minutes. The slurry was then clarified by centrifugation at 1000×g for 3 minutes and 5 µl of the supernatant was analyzed by western blot or SDS-PAGE.

Tissue culture: NIH-C226, SK-MES-1 and SW900 squamous cell lung cancer cells and A549 lung adenocarcinoma cells were obtained from the American type culture collection (ATCC) and cultured according to their instructions. The identities of the cell lines were confirmed by Genetica DNA Laboratories (Cincinnati, Ohio). Pgrmc1 inhibition by small interferring RNA (siRNA) transfection and expression of a dominant-negative mutant has been described previously (Crudden et al. J Pharmacol Exp Ther 2006, 316:448-55), as has AG-205 treatment (Ahmed et al., 2010).

The methods for transfection with GFP-Pgrmc1 expression plasmid pRC77 have been described (Ahmed et al. J Biol Chem 2010) and the GFP-Pgrmc1-D120G mutant was sub-cloned in the same manner as pRC77 from plasmid pRC45 (Crudden et al J Pharmacol Exp Ther 2006), resulting in plasmid pRC78. For adhesion assays, cells were transfected for 24 hours, transferred to chamber slides and incubated in serum-free medium for 5 days. The percent of green fluorescent cells attached to the substratum was scored in three separate fields for each transfected population.

Conditioned media from control and Pgrmc1 knockdown A549 NSCLC cells were generated by incubating cells in serum-free DMEM media for 24 hours. The media was then centrifuged and concentrated 10-fold (10 ml to 1 ml) using an Amicon Ultracel 10,000 molecular weight cut-off filter unit (Millipore, Billerica, Mass.). The concentrated medium was then incubated with 0.25 ml Separopore blue CL-6B slurry for 30 minutes and clarified by centrifugation at 1000×g for 3 minutes. H226 medium was concentrated similarly after incubating cells in serum-free medium for 24 hours. For fluorescent activated cell sorting (FACS), cells were stained with propidium iodide and analyzed as described (Mallory et al., Mol Pharmacol 2005, 68: 1747-56). Purified Pgrmc1 (Crudden et al., J Pharmacol Exp Ther 2006; 316:448-55) was added to cells and cultured in serum free media. For viability assays, cells were plated in 24 well dishes, washed with PBS and harvested by trypsinization and counted using a hemocytometer. Where indicated, cells were plated in 96 well dishes, and viability was measured by 3-(4,5-Dimethylthiazol-2-yl)-2,5-diphenyltetrazolium bromide (MTT) assay, as described (Hand and Craven. J Cell Biochem 2003, 90:534-47).

Discussion

In the present study, it is shown that secreted Pgrmc1 is a biomarker for cancer, preferably SCLC and adenocarcinoma of the lung. In addition to its elevation in lung tumors, Pgrmc1 was also secreted by lung cancer cell lines and was elevated in the plasma of lung cancer patients. Finally, a role for Pgrmc1 in SCLC cell survival is demonstrated, and a potential therapeutic approach for SCLC is presented.

In SCLC, Pgrmc1 was highest in the patients with poorly differentiated tumors, which correlates with survival in some lung tumors (Ichinose et al. J Thorac Cardiovasc Surg 1995, 110:601-5. 47; Takise et al., Cancer 1988, 61:2083-8). Pgrmc1 was readily detectable in SCLC cell lines, where its localization pattern resembled that of secretory vesicles, and Pgrmc1 promoted cell proliferation in SCLC cells. There are limited therapeutic options for SCLC, and we found that a Pgrmc1 inhibitor called AG-205 (Ahmed et al., J Pharmacol Exp Ther 2010) inhibited SCLC growth.

Pgrmc1 is also over-expressed in AdcL. It was been shown that Pgrmc1 promotes proliferation, migration, tumor growth and tumor metastasis in lung adenocarcinoma cells and furthermore, these cells were efficiently targeted with AG-205 (Ahmed et al., J Pharmacol Exp Ther 2010). The present study is an initial indication that Pgrmc1 expression is elevated in a limited subset (40%) of patients, but that elevated Pgrmc1 expressing tumors represent a subset with particularly poor outcome. While this observation will require validation in a larger cohort of patients, these patients may be an attractive population for testing Pgrmc1 inhibitors in the future.

Pgrmc1 is related to the secreted protein neudesin/NENF (neuron-derived neurotrophic factor)/Spuf (secreted protein of unknown function), and neudesin binds to an unknown receptor on neurons and elevates Akt signaling (Kimura et al., J Neurosci Res 2005, 79:287-94; Kimura et al., J Biol Chem 2008, 283:4323-31; Kimura et al., J Neurochem 2010; 112:1156-67). Like its relatives, Pgrmc1 was secreted by cancer cells and was detected in the plasma of healthy patients and at elevated levels in the plasma of lung cancer patients. Furthermore, Pgrmc1 increased the proliferation of lung cancer cells, suggesting that it may have a direct pro-carcinogenic role in vivo. This is the first report of tumor-associated elevations in plasma Pgrmc1 levels. However, the assay that we employed required a purification step that was not possible in archived samples, and survival data were not available for this study. Future research will delineate the clinical parameters associated with the patients containing high plasma Pgrmc1 levels. The assay could also be improved with less intrusive enrichment steps.

Together, the results suggest that Pgrmc1 is a potential tumor and serum biomarker for lung cancer. Furthermore, in vitro results suggest that secreted Pgrmc1 is active in promoting proliferation, similar to its homologues, although a potential receptor for Pgrmc1 is not known. Plasma-associated biomarkers would be particularly helpful for patients at risk for developing lung cancer, and a blood test could be significantly less expensive and less harmful than imaging. Pgrmc1 is also a potential therapeutic target in lung cancer, and the detection of Pgrmc1 in plasma may offer a means of identifying these patients with a facile screen.

All publications and patent documents cited in this application are incorporated by reference in their entirety for all purposes to the same extent as if each individual publication or patent document were so individually denoted. By their citation of various references in this document Applicants do not admit that any particular reference is "prior art" to their invention.

TABLE I

Patient sample characteristics

Sample numbers

| | |
|---|---|
| Squamous lung cancers | 15 tumors, 15 non-malignant tissue |
| Adenocarcinomas | 15 tumors, 15 non-malignant tissue |

Gender

| | |
|---|---|
| Squamous lung cancers | 10 male/5 female |
| Adenocarcinomas | 10 male/5 female |

TABLE I-continued

Patient sample characteristics

Age

| | |
|---|---|
| Squamous lung cancers | 53-82, average 65 |
| Adenocarcinomas | 42-76, average 60 |

| | Adeno | Squamous |
|---|---|---|
| Stage | | |
| 1A | 6 | 2 |
| 1B | 1 | 5 |
| 2A | 0 | 1 |
| 2B | 2 | 4 |
| 3A | 1 | 1 |
| 3B | 2 | 0 |
| 4 | 2 | 0 |
| Differentiation | | |
| well | 2 | 0 |
| moderately | 7 | 4 |
| poorly | 5 | 11 |

I claim:

1. A method of facilitating the treatment of cancer in a test subject, the method comprising the steps of: (a) providing a body fluid sample from a test subject; (b) isolating exosomes from the body fluid sample; (c) measuring Pgrmc1 level in the exosomes by using an immunoassay, (d) comparing the level of Pgrmc1 level in the exosomes with a the level of Pgrmc1 in exosomes of a sample from a subject without cancer, and (e) treating the test subject having an elevated level of Pgrmc1 with chemotherapy, immunotherapy, radiation therapy, endoscopy, biopsy, or surgery.

2. The method of claim 1, wherein the subject is a human.

3. The method of claim 1 wherein the cancer is lung cancer, or head or neck cancer.

4. The method of claim 1, wherein the immunoassay is ELISA, immunoblotting, or flow cytometry.

5. The method of claim 1, wherein the body fluid is blood, plasma or serum.

6. The method of claim 1 wherein the elevated Pgrmc1 level is at least 2-fold greater than the level in the sample from the subject without cancer.

7. The method of claim 1, wherein the immunoassay uses a polyclonal or monoclonal antibody.

8. A method of detecting the presence of a cancer in a test subject and treating the test subject, wherein the test subject is suspected of having, or has a cancer, the method comprising: a) isolating exosomes from a bodily fluid sample from the test subject; contacting the exosomes with an antibody that specifically binds to Pgrmc1; b) detecting the level of protein in the exosomes that specifically binds the antibody; and, c) comparing the level of protein in the exosomes to the level of protein that specifically binds the antibody in exosomes of a comparable normal bodily fluid sample; wherein an elevated level of protein in the exosomes of the test sample relative to the exosomes of the normal sample is an indication of the presence of the cancer in the individual, wherein the level of protein is detected in step b) by an immunoassay and d) treating the test subject having elevated Pgrmc1 level as compared to the Pgrmc1 level in exosomes of the normal bodily fluid sample with chemotherapy, immunotherapy, radiation therapy, endoscopy, biopsy, or surgery.

9. The method of claim 8, wherein the antibody is a polyclonal or monoclonal antibody.

10. The method claim 8, wherein the bodily fluid is blood, serum, or plasma.

11. The method of claim 8, wherein the cancer is lung cancer, or head or neck cancer.

12. The method of claim 8, wherein steps (a)-(c) are repeated and wherein a difference in the level of Pgrmc1 in the samples of the test subject over time is indicative of progression or regression of the cancer.

13. A method for treating a subject suspected of having cancer, comprising detecting the level of Pgrmc1 in exosomes isolated from the bodily fluid sample from a test subject suspected of having cancer and comparing the detected level with a reference level, wherein a Pgrmc1 level in the exosomes of the sample of the test subject above the reference level is indicative of a higher risk of the test subject having cancer, wherein the detection of the level of the Pgrmc1 is performed using an immunoassay, and then administering chemotherapy, immunotherapy, radiation therapy, endoscopy, biopsy, or surgery to the test subject having Pgrmc1 leel above the reference level.

14. The method according to claim 13, wherein the body fluid is blood, plasma or serum.

15. The method according to claim 13, wherein the immunoassay is an ELISA.

16. The method of claim 14, wherein the cancer is lung cancer, or head or neck cancer.

17. The method according to claim 13, wherein the reference level is (a) the level of Pgrmc1 in a comparable bodily fluid sample from a subject who does not have cancer or (b) an average of Pgrmc1 in a comparable bodily fluid of subjects without cancer that is derived from population studies on subjects who did not develop cancer.

* * * * *

SEQUENCE LISTING

```
<160> NUMBER OF SEQ ID NOS: 1

<210> SEQ ID NO 1
<211> LENGTH: 12
<212> TYPE: PRT
<213> ORGANISM: Homo sapiens

<400> SEQUENCE: 1

Gln Pro Ala Ala Ser Gly Asp Ser Asp Asp Glu
1               5                   10
```